(12) United States Patent
Bradley

(10) Patent No.: US 6,950,704 B1
(45) Date of Patent: Sep. 27, 2005

(54) USE OF ER SIGNAL VARIABILITY FOR FUSION DETECTION AND RESPONSE IN VENTRICULAR AND ATRIAL AUTOCAPTURE ALGORITHMS

(75) Inventor: Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 663 days.

(21) Appl. No.: 10/000,052

(22) Filed: Nov. 1, 2001

(51) Int. Cl.[7] .................................................. A61N 1/36
(52) U.S. Cl. ...................................................... 607/28
(58) Field of Search ............................... 600/508–510, 600/521; 607/4, 9, 27–28

(56) References Cited

U.S. PATENT DOCUMENTS

| | | | |
|---|---|---|---|
| 4,969,462 A | 11/1990 | Callaghan et al. ..... | 128/419 PG |
| 5,184,615 A | 2/1993 | Nappholz et al. ..... | 128/419 PG |
| 5,350,410 A | 9/1994 | Kleks et al. ................... | 607/28 |
| 5,391,192 A * | 2/1995 | Lu et al. ........................ | 607/28 |
| 5,411,533 A | 5/1995 | Dubreuil et al. .............. | 607/28 |
| 5,716,383 A | 2/1998 | Kieval et al. ................... | 607/9 |
| 5,749,906 A | 5/1998 | Kieval et al. ................... | 607/9 |
| 5,836,984 A * | 11/1998 | Obel .............................. | 607/9 |
| 5,861,013 A | 1/1999 | Peck et al. ..................... | 607/28 |
| 5,871,512 A | 2/1999 | Hemming et al. ............. | 607/28 |
| 6,038,474 A | 3/2000 | Zhu et al. ....................... | 607/9 |
| 6,192,275 B1 | 2/2001 | Zhu et al. ...................... | 607/28 |
| 6,275,734 B1 | 8/2001 | McClure et al. .............. | 607/27 |
| 6,324,427 B1 * | 11/2001 | Florio .......................... | 607/28 |
| 6,731,985 B2 * | 5/2004 | Poore et al. ................... | 607/28 |

FOREIGN PATENT DOCUMENTS

| | | | | |
|---|---|---|---|---|
| EP | 0870516 A2 | 3/1998 | ............ | A61N 1/37 |
| EP | 0870516 A3 | 3/1998 | ............ | A61N 1/37 |
| EP | 0904802 A2 | 8/1998 | ............ | A61N 1/39 |
| EP | 0904802 A3 | 8/1998 | ............ | A61N 1/39 |
| EP | 1023919 A2 | 1/2000 | ............ | A61N 1/37 |
| EP | 1023919 A3 | 1/2000 | ............ | A61N 1/37 |

* cited by examiner

*Primary Examiner*—Kennedy Schaetzle
*Assistant Examiner*—Kristen Mullen

(57) ABSTRACT

An implantable cardiac stimulation device is equipped to differentiate fusion beats, intrinsic activity, and evoked responses. The device optionally responds to improve cardiac activity.

33 Claims, 8 Drawing Sheets

USE OF ER SIGNAL VARIABILITY FOR FUSION DETECTION AND RESPONSE IN VENTRICULAR AND ATRIAL AUTOCAPTURE ALGORITHMS

CROSS-REFERENCE TO RELATED APPLICATIONS

This application is related to copending U.S. patent application Ser. No. 09/952,458, filed Sep. 10, 2001, entitled METHOD AND DEVICE FOR ENHANCED CAPTURE TRACKING BY DISCRIMINATION OF FUSION BEATS.

TECHNICAL FIELD

The present invention generally relates to methods and systems for providing cardiac pacing therapy. More particularly, the invention concerns methods and implantable stimulation devices for detecting fusion and/or loss of capture and responding thereto.

BACKGROUND

A goal of cardiac pacing therapy is to "capture" heart tissue, typically through administration of an electrical stimulus, e.g., a pacing pulse. Capture is achieved when an applied stimulus causes depolarization (contraction) of the heart's myocardial tissue. The stimulation-capture process allows for therapeutic management of various cardiac functions. For example, abnormal heart tissue contractions, known as arrhythmias, which include bradycardia (slow heart rate), tachycardia (fast heart rate), any markedly irregular rhythm, blocks and/or the presence of premature contractions, are manageable through use of stimulation-capture therapies.

Arrhythmias are often problematic and interfere with a heart's normal pumping function. In a normal heart, a pump cycle beings with a natural (or intrinsic) stimulus originating at the sinoatrial node, which then travels to intranodal atrial conduction tracts and the Bachmann's bundle and causes the atria to contract and pump blood into the ventricles. The stimulus next travels to the atrioventricular node, the Bundle of His, and the Purkinje system where the stimulus causes simultaneous contraction of the right ventricle, which pumps deoxygenated blood to the lungs through the pulmonary artery, and the left ventricle, which pumps oxygenated blood to the body through the aorta, the body's main artery. In an arrhythmic heart, the stimulation process is corrupt and capable of disabling the heart's pumping action. Pacing therapy seeks to terminate or overcome arrhythmic processes and allow the heart to function normally.

One method of terminating an arrhythmic process involves delivering a single cardioversion level electrical stimulus to the heart. After the stimulus, if the heart does not return to a satisfactory intrinsic rate, or an intrinsic beat is not established, then pacing therapy may continue on a beat-by-beat basis. In most beat-by-beat therapies, an implantable device monitors the heart and then determines whether a pacing stimulus is needed. In such therapies, a situation calling for a stimulus is the absence of intrinsic stimulation. An effective beat-by-beat pacing device therefore includes features to determine the need for a stimulus, to deliver a stimulus in a timely manner, and to ensure that a stimulus does not greatly exceed the energy level required to capture the heart. Most implantable stimulation devices operate on a limited power supply; thus, the features to determine the need for a stimulus and to control the power thereof act to prolong the life of the device. The determination and timely delivery features are useful in avoiding a condition known as fusion.

Fusion is commonly defined as cardiac depolarization that occurs in response to both an intrinsic stimulus and an applied electrical stimulus with cardiac depolarization (atrial or ventricular) resulting from more than one focus, e.g., two foci, one corresponding to the intrinsic stimulus and one corresponding to the applied stimulus. Evidence of fusion appears in polarization changes of active cardiac tissue, which can be sensed through electrodes placed on or within the heart. The measured or recorded signal from such electrodes is generally referred to as an intracardiac electrogram (IEGM). An IEGM provides valuable information as to the functioning of a patient's heart. For example, recordation of intrinsic ventricular depolarization results in a prominent IEGM waveform, classified as the QRS complex or R-wave. R-wave characteristics, as seen in an IEGM, reflect the presence of polarization changes resulting from both intrinsic and non-intrinsic activity. Because fusion is a combination of intrinsic and non-intrinsic activity, fusion often results in a distorted IEGM R-wave (QRS complex).

Fusion includes the terms "fusion beat", wherein an applied stimulus is delivered just prior to the arrival at the electrodes of an intrinsically generated and propagating R-wave, which affects the ventricular depolarization.

U.S. Pat. No. 5,836,984, entitled "Heart stimulating device", to Obel, assigned to Pacesetter AB, issued Nov. 17, 1998 ('984 patent), discusses pacemakers of the inhibition type wherein IEGM signals are sensed via a lead and electrode arrangement. Intrinsic and stimulated QRS waves in the IEGM signals are monitored by sensing circuitry in the pacemaker. According to the '984 patent, as long as intrinsic QRS complexes are detected at an acceptable rate by the sensing circuitry, the pacemaker inhibits stimulation. At each detected intrinsic QRS complex, a timer is started in the pacemaker. If no new QRS complex is detected within a predetermined basic interval of the timer, a stimulation pulse to the heart is emitted by a pulse generator in the pacemaker.

A problem noted by the '984 patent involves QRS complex detections that are performed after a bandpass filter, which delays the IEGM signals. In this situation, if an intrinsic QRS complex occurs immediately before the end of a basic escape interval (period between a sensed cardiac event and the next stimulation pulse), it will not be noticed before the next stimulation pulse is delivered. Consequently, when the next stimulation pulse is delivered, the pacemaker will have difficulties in detecting the QRS complex and, as a result of the non-detection, the pacemaker may react by increasing its output energy, even though such an increase is not needed. The '984 patent suggests that problems become more severe if the intrinsic heart rhythm is somewhat faster than that of the pacemaker and that a continuous state of this type could be avoided by using so-called hysteresis.

Hysteresis is a programmable feature available in some pacemakers that allows programming of a hysteresis escape rate (associated with the escape interval) that is lower than the programmed base rate (rate of stimulation pulses in the absence of intrinsic activity). Hysteresis may be accomplished by prolonging the pacing interval (time period between consecutive stimulation pulses without an intervening sensed event) following a sensed intrinsic beat.

The problem discussed in the '984 patent can lead to a higher energy consumption rate than necessary because the heart stimulating device emits pulses that are not required. Also, the energy of the stimulation pulses may erroneously be set higher than necessary. An excessively high energy consumption will cause premature depletion of the battery of the stimulation device resulting in higher risk and inconvenience to the patient. Thus, a need exists for stimulation devices that are capable of distinguishing between a true capture failure and a fusion beat.

Accordingly, there is a need for pacing therapies that better classify capture and fusion events.

SUMMARY

An exemplary implantable cardiac stimulation device includes a method of obtaining information related to cardiac depolarization or cardiac contraction, integrating the information to provide a value, comparing the value with a parameter, and implementing a technique in response to the comparing, for example, a capture technique or a fusion avoidance technique. Of course, the method may implement more than one technique. Such a device optionally senses and/or receives information from a sensor, such as an electrode positioned in the heart. According to the exemplary method, the device integrates and/or derives the information over time. For example, an electrode may provide voltage information over time, which upon integration yields an integral value and upon derivation yields a derivative value.

Where the method instructs a device to integrate information over time, the integration may start at the onset of cardiac depolarization and end at a baseline potential. The device may also derive information related to cardiac polarization, for example, provide a derivative of a voltage with respect to time. The derivation optionally occurs over a time interval, wherein the device can determine the maximum positive, negative, and/or absolute value derivative.

In this exemplary method, the parameter optionally comprises a statistical parameter. Statistical parameters include statistics such as, but not limited to, sample mean and standard deviation. A user may input the statistical parameter, or alternatively, the device processes information to provide a statistical parameter. Of course, the method optionally uses a combination of both user input and device processing to generate the parameter. For example, a user may input a factor, such as a number between approximately 1 and approximately 6. The device may then multiply a standard deviation by this factor and use the resulting product in combination with other information to generate a parameter or parameter range.

According to this exemplary method, the statistical parameter is optionally based on historic information related to cardiac depolarization. When based on historic information, the method can store and update the statistical parameter and/or recalculate a statistical parameter based on a combination of stored information (or values) and newly obtained information (or values).

The exemplary method optionally uses a probability or probabilities to determine a parameter. For example, the method can store a plurality of values, determine a probability distribution and then select a parameter corresponding to the probability of a value occurring. Of course, a parameter range would correspond to a range of probabilities and a range of values. Thus, the device and method can manage pacing therapy on the basis of probability, which may increase predictability of the power supply life.

Also suitable for use with an implantable stimulation device is a computer-readable media having computer-readable instructions thereon which, when executed by a programmable stimulation device, cause the stimulation device to execute the aforementioned exemplary method, other methods described herein and/or equivalents thereof.

In another exemplary method, an implantable stimulation device is operated to obtain information related to cardiac depolarization using at least one sensor, to process the information using a module to provide a value, to compare the value with at least one parameter using a microcontroller, and to implement a technique in response to the comparing using the stimulation device wherein the technique includes a capture technique and/or a fusion avoidance technique.

According to this method, the processing includes integrating using an integration module and/or deriving using a derivation module. Further, the at least one parameter optionally comprises a statistical parameter, for example, a statistical parameter based on historic information related to cardiac depolarization. The at least one parameter may also include a parameter corresponding to a probability.

According to various exemplary methods disclosed herein, and equivalents thereof, a device obtains information and uses that information to set limits and to determine whether to implement techniques such as, but not limited to, fusion avoidance techniques and/or capture techniques. For example, in one exemplary method, a device is operated to obtain information related to cardiac depolarization; to process the information to provide at least one value, the at least one value comprising a value selected from the group consisting of integral values and derivative values; to repeat the obtaining and the processing to provide a plurality of values; to determine a parameter from the plurality of values, the parameter comprising a statistic; to obtain additional information related to cardiac depolarization; to process the additional information to provide at least one additional value; to compare the at least one additional value to the parameter; and to implement a technique in response to the comparing.

A particular cardiac stimulation device for use with various methods described herein includes a sensor to obtain information related to cardiac depolarization and a processor operably coupled to the sensor. In this particular device, the processor is configured to determine a value from the information (e.g., integral values and derivative values), to determine a parameter from the information (e.g., a statistic), and to optionally compare the value and the parameter and/or to implement a technique (e.g., fusion avoidance techniques and/or capture techniques). The parameter may also correspond to a probability.

In another exemplary device, suitable for use with various methods described herein, the device includes sensing means for obtaining information related to cardiac depolarization; processing means for determining a value from the information (e.g., integral value and/or derivative value) and for determining a parameter from the information (e.g., a statistic); and optionally comparing means for comparing the value and the parameter. The parameter may also correspond to a probability.

This approach, as discussed herein, extends beyond that contemplated by traditional pacing therapies in that integrals, derivatives, statistics, and/or probabilities are optionally used. Further, according to various examples, user input is minimized due to limits being determined on the basis of statistics and/or probabilities.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Devices, methods and/or computer-readable media disclosed herein allow for pacing therapy in response to information related to cardiac activity. The devices, methods, and/or computer-readable media utilize the information as integrals, derivatives, statistics and/or probabilities to avoid fusion and/or effectuate capture.

Exemplary Stimulation Device

The techniques described below are intended to be implemented in connection with any stimulation device that is configured or configurable to stimulate or shock a patient's heart.

Figure 1:
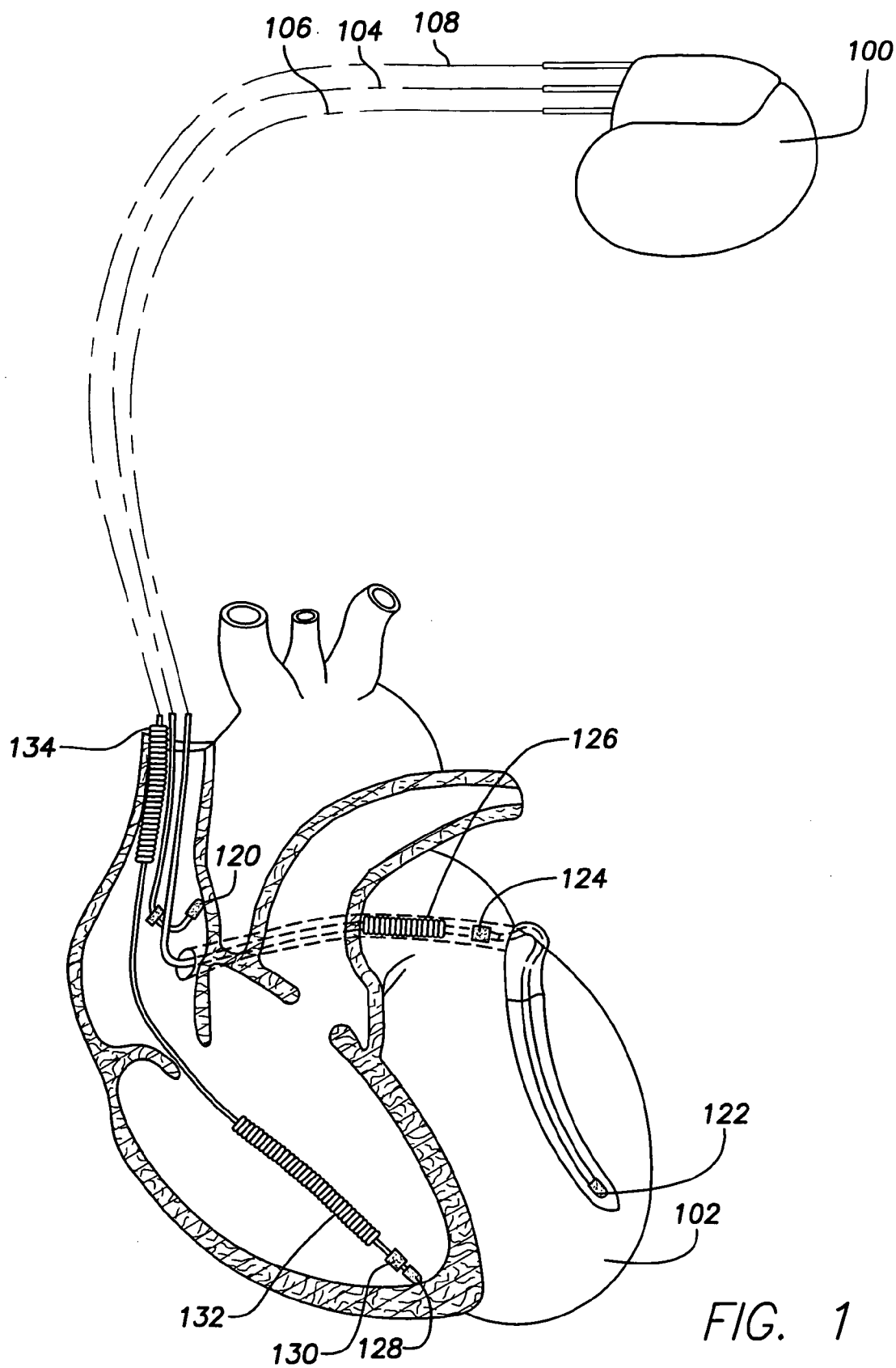
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
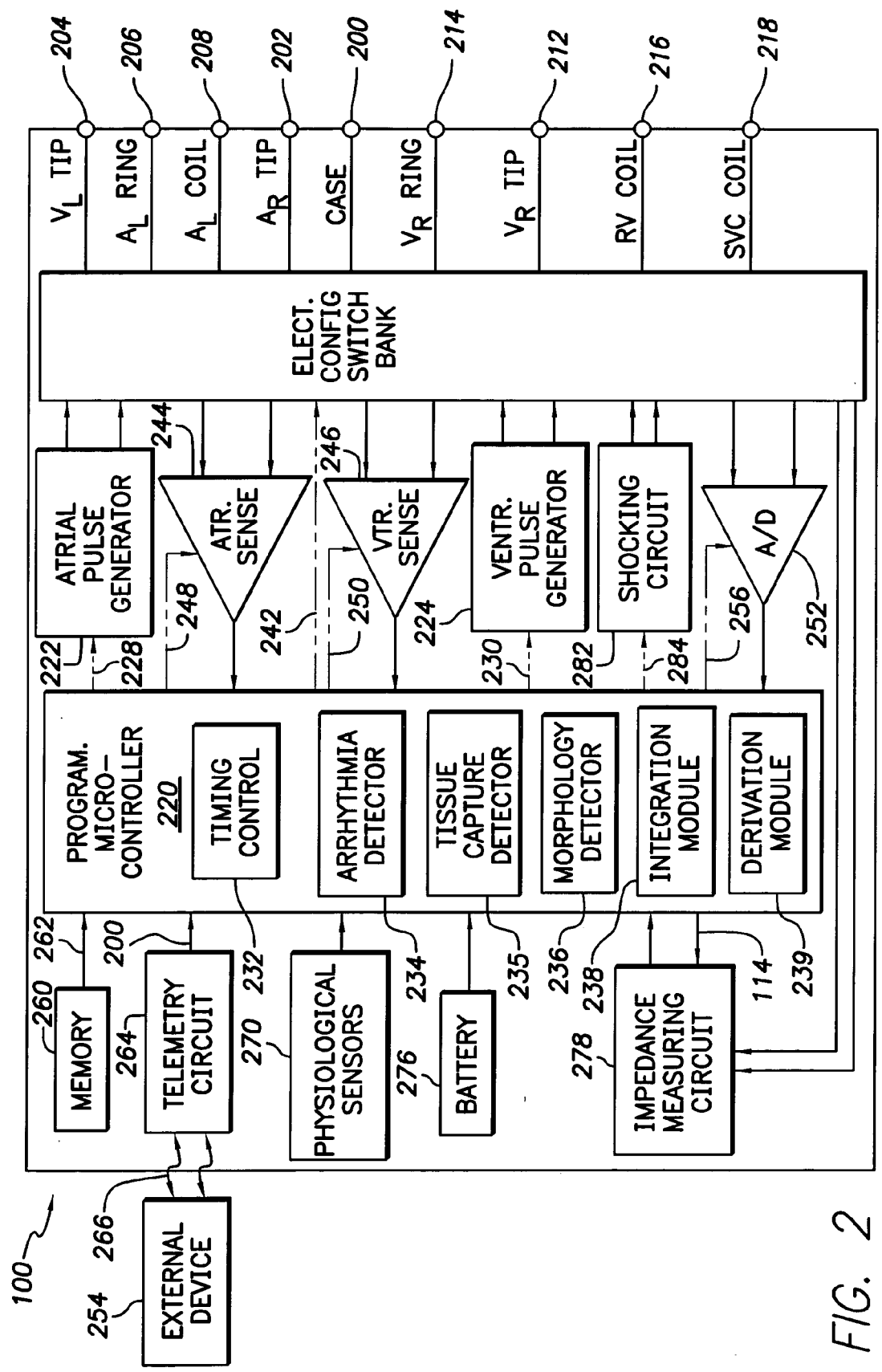
FIG. 2 is a functional block diagram of a multi-chamber implantable stimulation device illustrating basic elements that are configured to provide cardioversion, defibrillation, and pacing stimulation in four chambers of the heart. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, an orthostatic compensator, and a minute ventilation (MV) response module, the latter two optionally operating within the microcontroller 220. These components can be utilized by the stimulation device 100 for determining desirable times to administer various therapies, including those to reduce the effects of orthostatic hypotension, as will become more apparent below. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation. For a complete description of a typical sensing circuit, the reader is directed to U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, the reader is directed to U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 (or other system or circuitry, e.g., atrial sensing circuitry 244 and ventricular sensing circuitry 246) may be coupled to the microcontroller 220, or other detection circuitry, for analyzing the obtained information to detect an evoked response from the heart 102 in response to an applied stimulus, thereby aiding in detection of tissue "capture." Capture occurs when an electrical stimulus applied to the heart is of sufficient energy to depolarize the cardiac tissue, thereby causing the cardiac tissue (e.g., myocardial tissue) to contract. For example, the microcontroller 220 is capable of analyzing obtained information to detect a depolarization signal during a window following a stimulation pulse, the presence of which indicates that some degree of tissue capture has occurred. In one implementation, the microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window. The information obtained through the data acquisition system 252 is then analyzed to determine whether and/or to what degree tissue capture has occurred. This analysis optionally uses signal amplitude and/or gradient (e.g., voltage over time) to ascertain whether tissue activation has occurred and, if so, to ascertain a corresponding activation time or times. Such results are useful in determining, for example, pacing pulse regimens and/or whether to administer cardioversion level stimuli.

To facilitate detection of tissue capture, the microcontroller 220 comprises a dedicated tissue capture detector 235. This detector 235 is capable of analyzing information obtained through the sensing circuits, 244 and 246, and/or the data acquisition system 252. The detector 235 analyzes the sensed information to produce a result, such as, activation time. Of course, the detector 235 is also capable of noting whether activation has occurred during any given time period. The detector 235 or other microprocessor features can use these results to determine pacing pulse regimens and/or other actions.

Capture detection may occur on a beat-by-beat basis, a sampled basis, or other suitable basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is last obtained is known as the capture threshold. Thereafter, a safety margin or factor is added to the capture threshold.

The implementation of capture detection circuitry and algorithms are well known. See, for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), all of which are hereby incorporated herein by reference. The type of capture detection system used is not critical to the described implementations.

As already mentioned, the data acquisition system 252 (or other system or circuitry, e.g., atrial sensing circuitry 244 and ventricular sensing circuitry 246) may be coupled to the microcontroller 220, or other detection circuitry, for analyzing obtained information concerning cardiac activity. FIG. 2 shows an integration module 238 and a derivation module 239 coupled to the microcontroller 220. The integration module 238 and derivation module 239 optionally operate under control of the microcontroller 220. In such an instance, the microcontroller 220 controls the operation of the two modules through software/firmware. The integration module 238 and derivation module 239 accept digital and/or analog information and output digital and/or analog information. In another configuration, the integration module 238 and derivation module 239 optionally operate in an analog manner wherein, for example, integration and derivation are performed using analog components. The microcontroller 220 and/or other components can access information output from the integration module 238 and/or derivation module 239. Of course, a single module may also be used to perform all of the functions of the integration module 238 and derivation module 239.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.), now U.S. Pat. No. 6,275,734, which patents are incorporated herein by reference.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium derivative battery chemistries.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 Joules), moderate (0.5–10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Sensing Cardiac Activity

In one exemplary process, an implantable device is programmed to sense cardiac activity. For example, consider the device 100 shown in FIGS. 1 and 2. A lead (104, 106, or 108) positioned in a chamber of the heart, and connected to the device 100, carries a signal indicative of cardiac activity. The device 100 receives the signal, which consists of a time varying voltage. To understand better the nature of the signal, an illustration appears in FIG. 3A, presented as plots of voltage versus time.

Figure 3A:
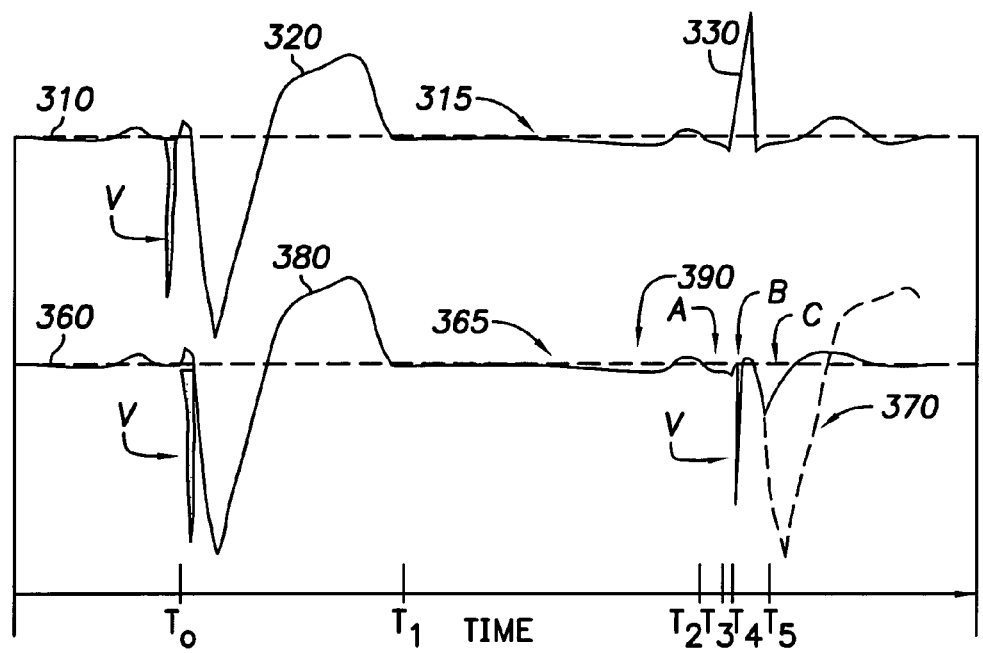
FIGS. 3A through 3E are illustrations of surface and intracardiac electrograms for evoked, fusion, and intrinsic cardiac activity.
Figure 3B:
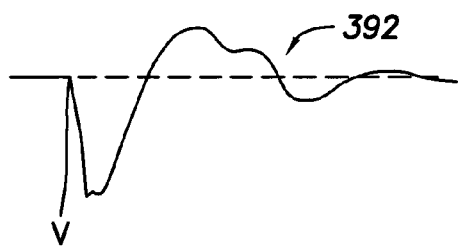
Figure 3C:
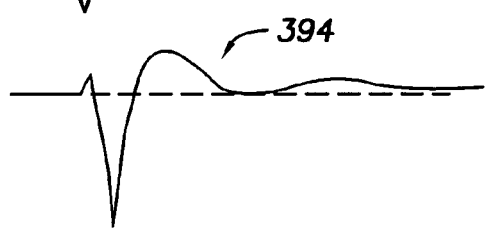
Figure 3D:
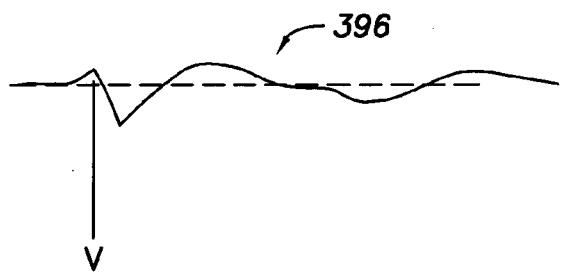
Figure 3E:
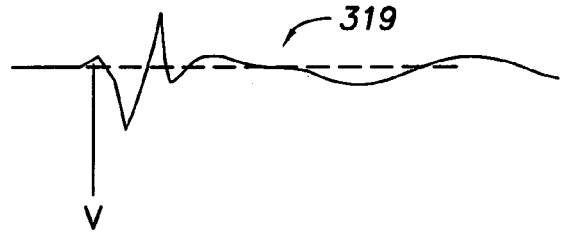

Referring to FIG. 3A, two waveforms 310, 360 are shown wherein voltage varies with respect to time. The upper waveform 310 includes a ventricular evoked response waveform 320 between times $t_0$ and $t_1$ in response to an applied stimulusV and a waveform 330 between approximately times $t_2$ and $t_5$ in response to an intrinsic stimulus. The response 320 is characteristic of an IEGM waveform, while the response 330 is characteristic of a surface ECG waveform.

The second waveform 360 includes an evoked response waveform 380 between times $t_0$ and $t_1$ in response to an applied stimulusV (identical to response 320) and a waveform 390 between approximately times $t_2$ and $t_5$ in response to both an applied stimulusV and an intrinsic stimulation (i.e., an example of a fusion beat). Both waveforms 380 and 390 are characteristic of IEGM waveforms. Waveform 390 also includes (as a dotted line) a plotted representation of an expected signal 370 for an applied stimulus response in the absence of an intrinsic stimulus. The expected signal 370 facilitates a comparison between the signal for the combined response and the signal for the applied stimulus response.

Referring now to FIGS. 3B through 3E, there are shown additional waveforms 392, 394, 396, and 398 that display various intrinsic, evoked, and fusion IEGM waveforms. For example, waveform 392 is illustrative of a unipolar-sensed evoked response resulting from a ventricular stimulation pulse. Waveform 392 depicts a large paced depolarization integral (PDI) and a medium slope of the positive-going waveform (DMAX).

Waveform 394 is illustrative of a unipolar-sensed intrinsic R-wave, and is characterized by a small to medium PDI and large DMAX. Waveform 396 is illustrative of a unipolar-sensed fusion waveform in the ventricle, which exhibits small PDI and small DMAX (sometimes referred to as a "black hole fusion"). Waveform 398 is illustrative of a unipolar- sensed fusion waveform in the ventricle, which also exhibits small PDI, but with high DMAX.

While the waveforms illustrated in FIGS. 3A through 3E depict ventricular activity, it will be understood by those skilled in the art that the invention is applicable to atrial activity as well.

Integral Methods

In one exemplary method, a device 100 acquires cardiac activity data, rectifies and integrates the cardiac activity data, and determines a therapy based on the integrated data. In this method, the device 100 includes an integration module 238 capable of integrating a signal with respect to time, such as, a voltage signal with respect to time. With reference to FIGS. 3A through 3E, the time interval for the integral typically lies within a window spanning ventricular depolarization. In one embodiment, a suitable time interval extends between the voltage crossing a baseline voltage 315, 365 and the voltage returning to the baseline voltage 315, 365. Thus, the resulting integral represents the total area of the IEGM plot.

Referring again to FIG. 3A, and particularly waveform 390, a similar time interval may be defined wherein the interval starts at a time where the voltage crosses a baseline voltage value 365 and ends at a time where the voltage returns to a baseline voltage value 365.

As mentioned with reference to FIGS. 3A through 3E, waveform 390 meets the criteria set forth for fusion: (i) the applied stimulus affected the ventricular depolarization, in part because, (ii) the applied stimulus was delivered just prior to a measured intrinsic depolarization. More importantly, for purposes of this method, the voltage—time integral of the waveform 390 differs substantially from the voltage—time integral of the applied stimulus evoked waveforms (e.g., 320 or 380), as readily seen by a visual comparison of the complexes. Note that this difference does not depend heavily on the time interval of the fusion integral. Referring to FIG. 3A, even if the interval spanned from the beginning of interval A to the end of interval C, the magnitude of the integral of the applied stimulus evoked response (e.g., see waveform 320, 380) would still be greater than that of the fusion response. Therefore, according to this exemplary method, a device may set and/or adjust the time interval in a variety of manners. For example, a device can trigger the start of an integral time interval on the basis of a set time, a set voltage value, a voltage derivative value, etc. A device can trigger the end of the time interval on a similar basis, or alternatively, on the basis of a timer that begins to run at the start of the interval.

Throughout this disclosure, the integral method optionally uses absolute values of integrals. Thus, if a comparatively small integral value results (i.e., small in comparison to the absolute value of an evoked response integral over the Q-S interval and further in comparison to the absolute value of a fusion integral), then the device may determine that loss of capture has occurred.

The integral methods described above allow a device to classify cardiac activity as fusion, cardiac capture, and/or loss of capture. Suitable integration techniques for use in the aforementioned methods include, but are not limited to, paced depolarization integration (PDI) techniques and equivalents thereof. Once a device has integrated a signal, then a determination process can follow to determine an appropriate course of action. Typically, the determination process includes a classification of cardiac activity.

Derivative Methods

In another exemplary method, a device 100 acquires cardiac activity data, derives a time derivative of the data, and determines a therapy based on the time derivative. In this method, the device 100 includes a derivation module 239 capable of deriving a time derivative of a signal, such as, a time varying voltage signal. With reference to FIG. 3, the voltage derivative with respect to time typically lies within a window spanning ventricular depolarization. In one illustrative embodiment, the method determines the maximum value of the positive-going slope of the waveform, which is used as the derivative (or DMAX) value.

As shown in waveforms 320 and 380 of FIG. 3A, an evoked response exhibits a prolonged positive change in voltage. A device 100 may derive one or many derivatives of the voltage signal with respect to time over this interval and, in the case of many, the device 100 may further determine a maximum derivative (DMAX) and/or "local" maximum derivative. A device 100 may also derive a derivative for a signal coming from a fusion beat, an intrinsic beat, and/or a lost capture response.

Referring to the fusion waveform 390 of FIG. 3A, a device 100 may derive a plurality of derivatives over a suitable interval spanning from the beginning of the non-baseline voltage until the return to baseline voltage, and then determine the maximum positive derivative. Note that the derivative for waveform 390 exceeds that of the evoked response waveforms 320 and 380. Thus, one factor that may be used by device 100 to classify a response as a fusion response is whether a maximum positive derivative exceeds that of an evoked response's maximum positive derivative (or some preset threshold value).

However, due to variability inherent in fusion, the maximum positive derivative of a fusion response may fall below that of an "average" evoked response. In most instances, if a maximum positive derivative of a fusion response falls below the maximum positive derivative of an evoked response, it is likely to fall well below the average, and can be differentiated by defining a second threshold value. Thus, the only fusion events that remain unclassifiable by this derivative method are those that have a maximum positive derivative approximately equal to that of an evoked response. A method that also relies on an integral technique can compensate for this deficit and, of course, other techniques may also be used to compensate.

When a maximum positive derivative falls well below that of an average evoked response and to a value close to zero (or, e.g., more than a magnitude less than the average), a device 100 can further classify such cardiac activity as a loss of capture.

The derivative methods described above allow a device to classify cardiac activity as fusion, cardiac capture, or loss of capture. Once a device has derived a derivative of a signal and/or determined a maximum from a plurality of derivatives, then a determination process can follow to determine an appropriate course of action. Typically, the determination process includes a classification of cardiac activity.

Statistical Methods

In addition to the integral methods and the derivative methods above, statistical methods can complement the processes discussed herein. For example, in one exemplary statistical method, a device 100 calculates a running average of integral and/or derivative statistics, including a sample mean (and/or mean, median, mode, etc.) and at least one variability parameter. Parameters that give an indication of variability include: standard deviation, variance, minima and maxima. Forgetting factors (weighting of data as a function of time, etc.) and other methods know to one of ordinary skill in the art of control systems are optionally implemented. All of the aforementioned statistics can be determined over a short and/or long duration and/or stored in memory of a device over a short and/or long duration. In particular, events of significance are optionally stored in memory. A more detailed discussion of statistical methods appears below with reference to FIGS. 5A–B and 7A–B.

Implementing Integral and/or Derivative Methods

Figure 4:
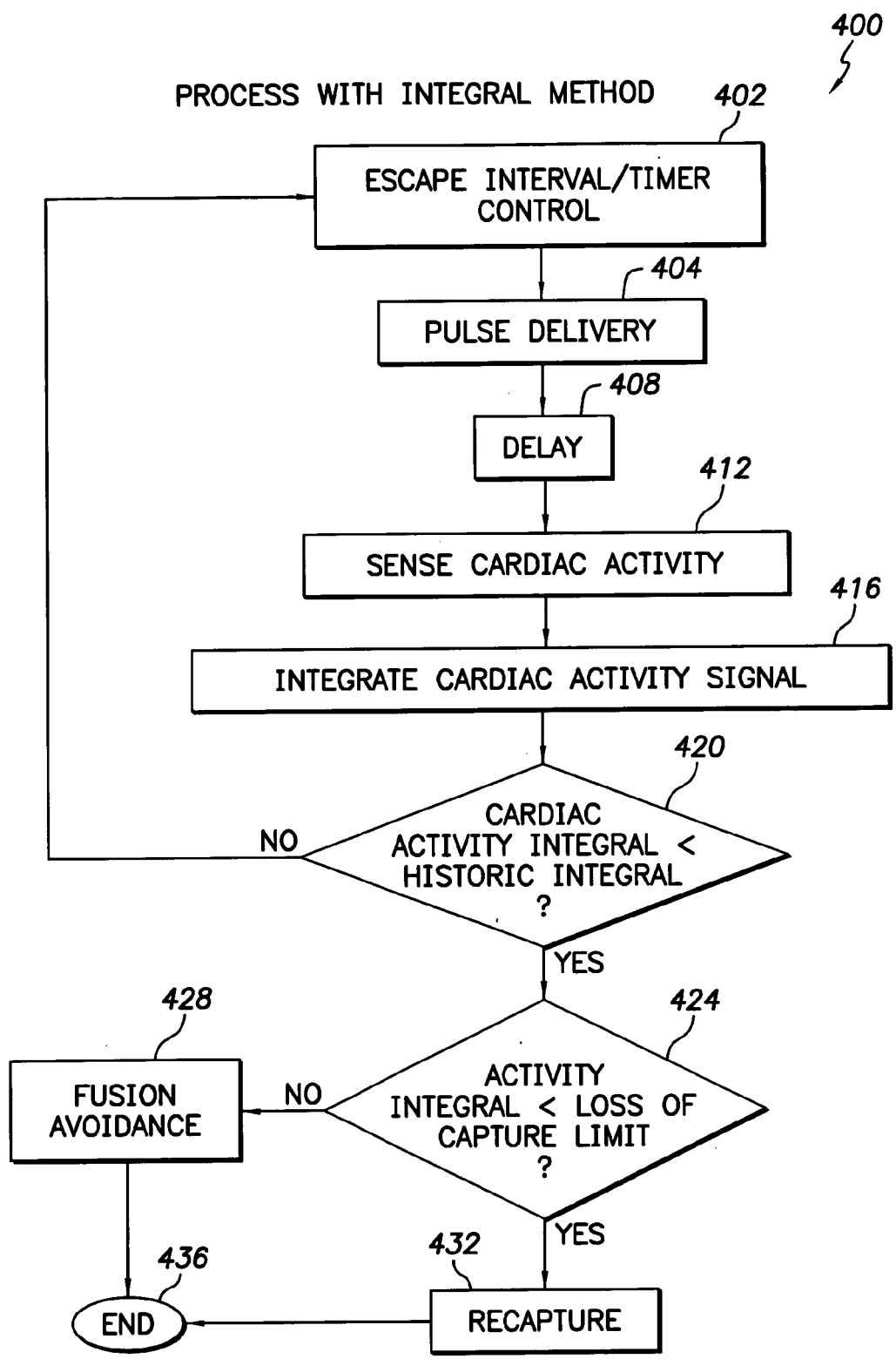
FIG. 4 is a functional block diagram of an integral process for detecting fusion and/or loss of capture and responding to the same.
Figure 6:
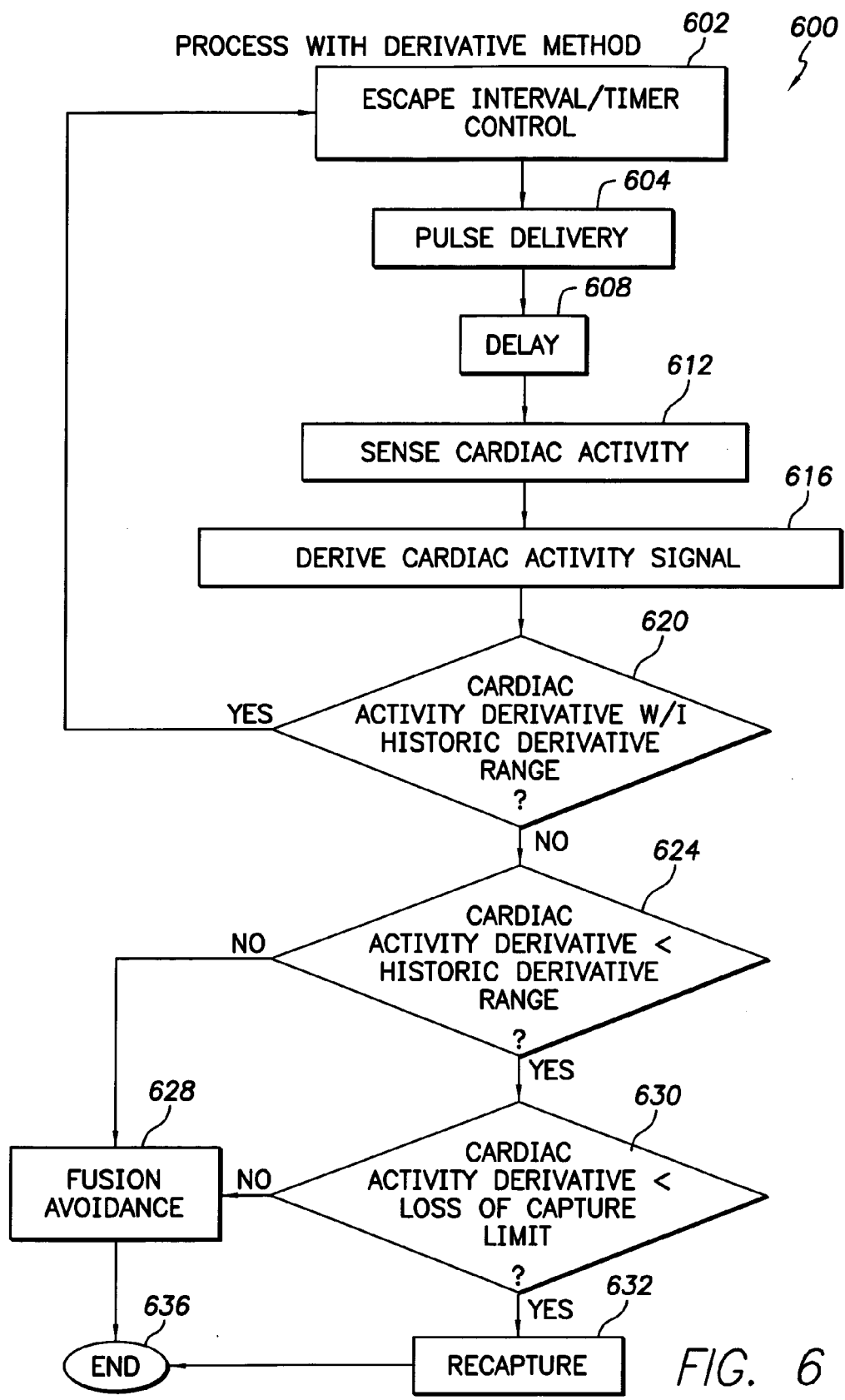
FIG. 6 is a functional block diagram of a derivative process for detecting fusion and/or loss of capture and responding to the same.

FIGS. 4 and 6 show exemplary processes using the aforementioned integral and/or derivative methods, with or without use of additional statistical methods. These methods can be implemented in connection with any suitably configured stimulation device. One specific and non-limiting example of a stimulation device was described above with respect to FIGS. 1 and 2.

In the flow diagrams of FIGS. 4 and 6, various algorithmic acts are summarized in individual "blocks". Such blocks describe specific actions or decisions that are made or carried out as the process proceeds. Where a microcontroller (or equivalent) is employed, the flow charts presented herein provide a basis for a "control program" or software/firmware that may be used by such a microcontroller (or equivalent) to effectuate the desired control of the stimulation device. As such, the processes are implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the inventive subject matter described herein includes not only stimulation devices when programmed to perform the acts described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

An exemplary process comprising an integral method 400 is described herein with reference to FIG. 4. Referring to FIG. 4, after an elapsed time corresponding to the pulse delivery rate determined by the timer control circuitry 232 at block 402, a pulse delivery block 404 delivers a pulse to a chamber of the heart. Following delivery, a delay block 408 delays sensing. The delay may correspond to a "blanking interval", which is an interval initiated by the delivery of a pulse during which the sense amplifier is temporarily disabled. Not all stimulation devices institute blanking periods, which are generally given in milliseconds and may be preset and/or programmable. After the delay, a sense block 412 commences sensing of cardiac activity. The signal sensed by the device may cover a pre-determined time interval or may cover a time interval determined in real time, e.g., triggered by certain events. An integrate cardiac activity signal block 416 follows the sense block 412; however, in an alternative process, the sensing and integration occur simultaneously wherein the signal is integrated by a circuit within the device upon sensing. In such a process, to provide a final integral value, the device stops sensing and/or stops directing the sensed signal to the integration circuit. In either process, the device optionally stores the integral value in memory.

To classify the nature of the cardiac activity, a comparison block 420 compares the cardiac activity integral from the integrate block 416 with a historic integral. The historic integral value optionally comprises an average of integral values for evoked response signals (see waveforms 320 and 380 of FIG. 3A). A device optionally comprises the ability to generate additional statistical information regarding historic integrals and other cardiac activity, as discussed in the above section on Statistical Methods. For example, comparison block 420 may compare the cardiac activity integral with an average historic integral minus a whole or a fractional number of standard deviations of the historic integral average. In an alternative process, the comparison block 420 compares the cardiac activity integral with a preset or programmed value.

Referring again to the comparison block 420, if the cardiac activity integral is greater than or equal to the historic integral, then the process 400 returns to the timing control block 232. However, if the cardiac activity integral is less than the historic integral, then another comparison block 424 compares the cardiac activity integral with a loss of capture limit, which has the same units of the cardiac activity integral. If the cardiac activity integral is greater than or equal to the loss of capture limit, then the process 400 enters a fusion avoidance block 428. The fusion avoidance block 428 implements one or a variety of fusion avoidance techniques, including, for example, pulse inhibition, positive or negative rate adjustment, and/or AV/PV hysteresis adjustment. The device implements fusion avoidance because an integral value that falls between the historic integral and the loss of capture limit indicates fusion. To conserve energy, the fusion avoidance block 428 optionally instructs the device to withhold pulse delivery, which is a method of fusion avoidance. As discussed above, the presence of fusion corresponds to intrinsic activity, which may alone be sufficient to capture the heart. Under such circumstances, an applied stimulus can waste energy and thereby unnecessarily drain the device's power supply. After the fusion avoidance block 428, the process 400 may terminate at a termination block 436. After termination, the device may simply sense cardiac activity to insure that the intrinsic activity maintains an adequate beat.

If, in the comparison block 424, the cardiac activity integral falls below the loss of capture limit, then a recapture process commences with a recapture block 432. After capture has been established, the process 400 optionally terminates at a termination block 436.

Figure 5A:
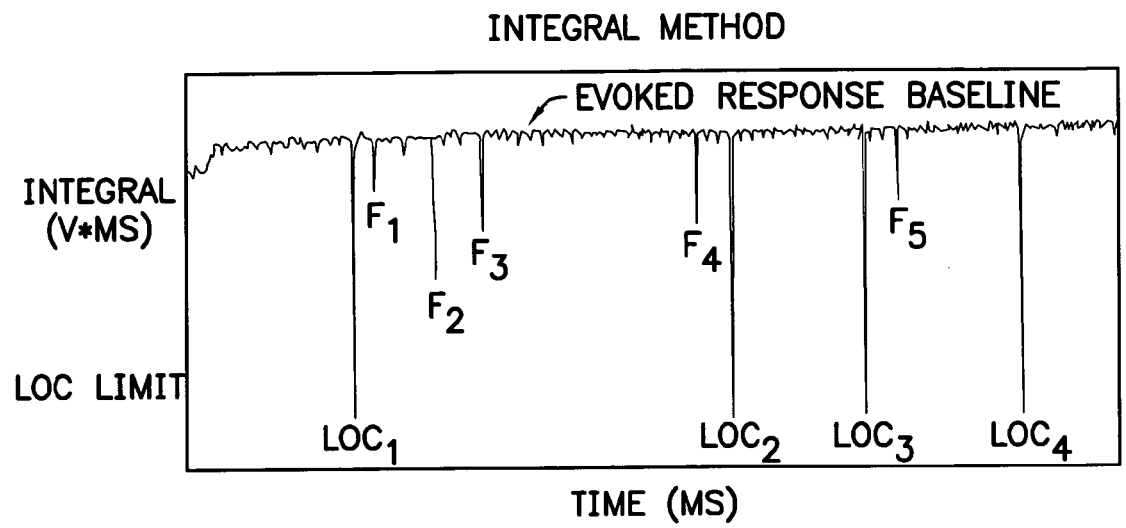
FIG. 5A is a plot of voltage times time versus time for an integral process.

FIG. 5A shows a plot of integral values versus time. The integral value for cardiac activity corresponding to evoked responses establishes a "baseline" (labled as Evoked Response Baseline); however, some upward drift has occurred over the period shown. Again, moving averages and/or the statistical methods can account for such "baseline" variations over time. This plot shows four loss of capture events (labeled $LOC_1$–$LOC_4$) and five fusion events (labeled $F_1$–$F_5$) that may call for fusion avoidance. The loss of capture events appear as integrals having values less than the loss of capture limit. The fusion events appear as integrals having values less than the baseline minus a standard deviation (or other measure) and greater than the loss of capture limit.

Figure 5B:
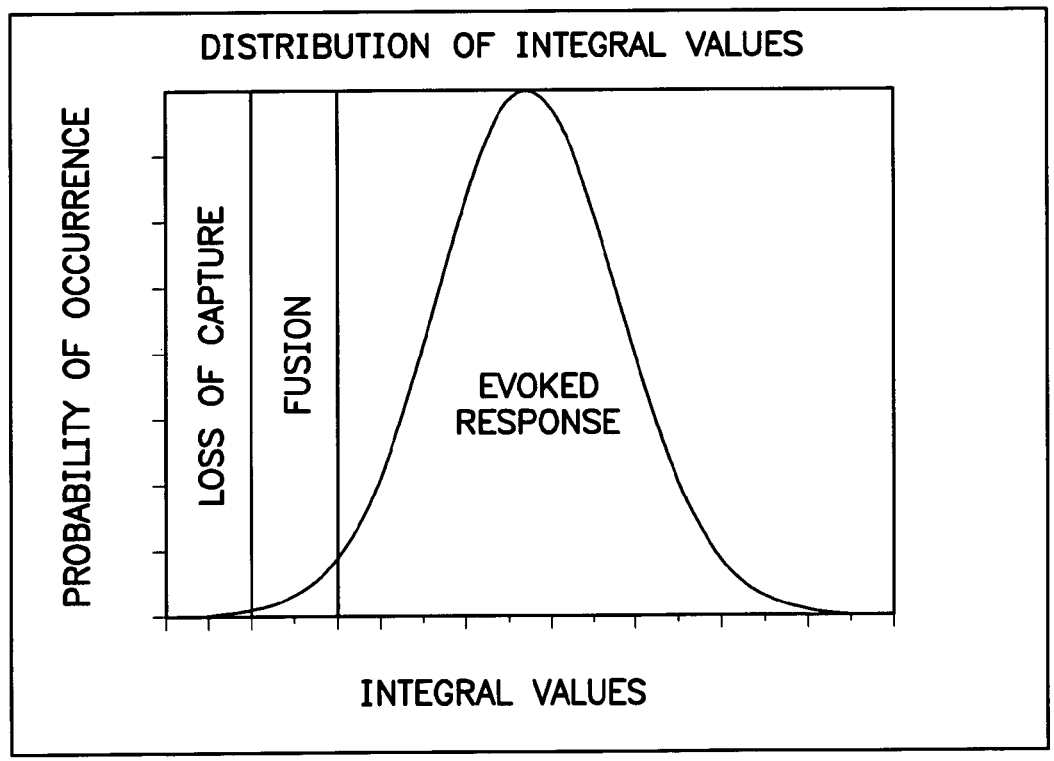
FIG. 5B is a probability distribution plot for integral values.

FIG. 5B shows a distribution of integral values, this distribution is for the purpose of illustration and does not correspond to the actual integral values of FIG. 5A. Actual distributions may under some circumstances have multimodal characteristics, for example, one "mode" corresponding to an evoked response and another "mode" corresponding to fusion. Devices and methods disclosed herein optionally comprise modules capable of using multimodal information to classify cardiac activity and/or determine a pacing therapy. While FIG. 5B shows a probability distribution, a device may rely on a histogram distribution and/or a probability distribution and a user or the device may set parameters (e.g., limits) based on probability and/or other statistical information. As shown, the distribution has three regions: Evoked Response; Fusion; and Loss of Capture. A device may adjust the boundaries between these regions or they may be preset. The boundary between the Fusion and Loss of Capture region corresponds to the loss of capture limit shown in FIG. 5A. A device may set the Fusion and Evoked Response boundary according to user input and/or sensed cardiac activity. Of course, adjustment of these boundaries may, in turn, determine a statistical probability of encountering Fusion or Loss of Capture.

A probability distribution of integral values (or parameters related thereto) may be unique to each patient and hence each patient may have unique boundaries that account for a plethora of health and/or lifestyle conditions, which may also account for power source limitations. Statistical methods related to probability allow a user or a device to determine a mode. The mode of a distribution corresponds to the value that occurs most frequently (note that a multimodal distribution has only a single mode). Often the mode is different than the median, the mean or the sample mean. The "median" is the value with half the values above it and half the values below it. The "mean" is the average in a traditional sense and it is analogous to the expected value (sum of the values weighted by their probabilities); whereas, "sample mean" is based on sample values.

For an integral method corresponding to the values shown in FIG. 5A, the distribution would not be symmetric, but rather skewed to the left (a tail to the left) due to fusion and loss of capture. In such an instance, one may expect the mean to be less than the median and the median less than the mode.

Methods disclosed herein optionally include statistical parameters such as variance and standard deviation. Generally, the standard deviation is the square root of the variance. The standard deviation represents an average "distance" of the individual sample "distances" from the mean of the samples. In addition, the standard deviation of the sample mean typically decreases in proportion to the square root of the number of samples (and the variance of the sample mean typically decreases linearly with added samples). Methods disclosed herein optionally maintain statistics (e.g., statistical parameters) based on a fixed number of samples—e.g., including running or moving statistics.

In one exemplary method, a device obtains information related to cardiac activity. The device integrates the information over a time interval to provide an integral value. Next, the device determines at least one statistical parameter based on the integral value. The device continues to obtain, integrate and determine until the statistical parameter satisfies a criterion or criteria. For example, a device may decide to implement the integral feature if the standard deviation of the samples falls below a limit. Alternatively, the device may decide to implement the integral feature if a running standard deviation exceeds a limit.

Another statistical method includes cumulative distribution functions. A device or a user may use a cumulative distribution function to determine the probability that an outcome (e.g., an integral value) will lie between two parameters (e.g., two integral values). For example, a device or a user may set fusion and loss of capture limits based on probabilities or a probability. According to such a statistical method, a device or user specifies an expected probability of loss of capture. The device or user then uses a distribution of historic information to determine the value that corresponds to that probability. The device then uses the determined value (or parameter) as a loss of capture limit and any integral value falling below that limit will be classified as loss of capture.

An exemplary process comprising a derivative method 600 is described herein with reference to FIG. 6. Referring to FIG. 6, after an elapsed time corresponding to the pulse delivery rate as determined by the escape interval/timer control circuitry 232 at block 602, a pulse delivery block 604 delivers a pulse to a chamber of the heart. Following delivery, a delay block 608 delays sensing. The delay may correspond to a "blanking interval", which is an interval initiated by the delivery of a pulse during which the sense amplifier is temporarily disabled. Not all stimulation devices institute blanking periods, which are generally given in milliseconds and may be preset and/or programmable. After the delay, a sense block 612 commences sensing of cardiac activity. The signal sensed by the device may cover a pre-determined time interval or may cover a time interval determined in real time, e.g., triggered by certain events. A derive cardiac activity signal block 616 follows the sense block 612; however, in an alternative process, the sensing and derivation occur simultaneously wherein the signal is derived by a circuit within the device upon sensing. In such a process, to provide a final derivative value, the device stops sensing and/or stops directing the sensed signal to the derivative circuit. In either process, the device optionally stores at least one derivative value in memory.

To classify the nature of the cardiac activity, a comparison block 620 compares a cardiac activity derivative, optionally a maximum positive derivative, from the derivative block 616 with a historic derivative value and/or a range about a historic derivative value. For example, the comparison block optionally compares the cardiac activity derivative with a historic derivative average plus or minus one standard deviation about the average. The derivative value optionally comprises an average of derivative values for evoked response signals over a Q-S interval (see QRS complexes 320 and 380 of FIG. 3). A device optionally comprises the ability to generate additional statistical information regarding historic derivatives and other cardiac activity, as discussed in the above section on Statistical Methods. For example, as already mentioned, comparison block 620 may compare the cardiac activity derivative with an average historic derivative plus and/or minus a whole or a fractional number of standard deviations of the historic derivative average. In an alternative process, the comparison block 620 compares the cardiac activity derivative with a preset or programmed value or values.

Referring again to the comparison block 620, if the cardiac activity derivative is within a range about the historic derivative, then the process 600 returns to the pulse delivery block 604. However, if the cardiac activity derivative is outside of the bounds, then another comparison block 624 compares the cardiac activity derivative to a historic derivative. If the derivative is greater than the historic derivative, then the process 600 enters a fusion avoidance block 628. The device optionally inhibits pulse delivery, a method of fusion avoidance, because a derivative value has exceeded the historic derivative average upper range. By withholding pulse delivery, this option conserves energy. As discussed above, the presence of fusion corresponds to intrinsic activity, which typically is sufficient to capture the heart. Under such circumstances, an applied stimulus can waste energy and thereby unnecessarily drain the device's power supply. After the fusion avoidance block 628, the process 600 may terminate at a termination block 636. After termination, the device may simply sense cardiac activity to insure that the intrinsic activity maintains an adequate beat.

Referring again to comparison block 600 if the cardiac activity integral is less than the historic derivative, then another comparison block 630 compares the cardiac activity derivative with a loss of capture limit, which has the same units of the cardiac activity derivative. If the cardiac activity derivative is greater than or equal to the loss of capture limit, then the process 600 enters a fusion avoidance block 628. The fusion avoidance block 628 implements one or a variety of fusion avoidance techniques, including, for example, pulse inhibition, positive or negative rate adjustment, and/or AV/PV hysteresis adjustment. The device implements fusion avoidance because a derivative value that falls between the lower range of the historic derivative and the loss of capture limit indicates fusion. After the fusion avoidance block 628, the process 600 may terminate at a termination block 636. After termination, the device may simply sense cardiac activity to insure that the intrinsic activity maintains an adequate beat.

If, in the comparison block 630, the cardiac activity derivative is less than the historic derivative loss of capture limit, then a recapture process commences with a recapture block 632. After capture has been established, the process 600 optionally terminates at a termination block 636.

Figure 7A:
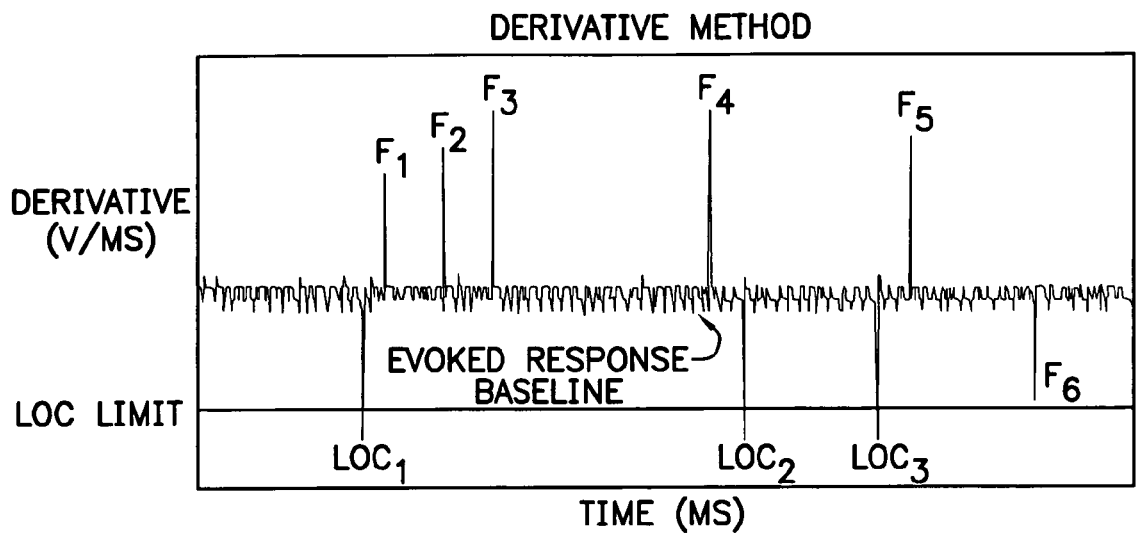
FIG. 7A is a plot of voltage divided by time versus time for a derivative process.

FIG. 7A shows a plot of derivative values versus time. The derivative value for cardiac activity corresponding to evoked responses establishes a "baseline" (labeled as Evoked Response Baseline). Again, moving averages and/or the statistical methods can account for most any variation in the "baseline" over time. This plot shows three loss of capture events (labeled $LOC_1$–$LOC_3$) and six fusion events (labeled $F_1$–$F_6$) that call for fusion avoidance. The loss of capture events appear as derivatives having values less than the loss of capture limit. The fusion events appear as five derivative values greater than an upper range about the historic derivative value and one derivative having a value less than the historic derivative value minus, e.g., a standard deviation (or other measure), and greater than the loss of capture limit.

Figure 7B:
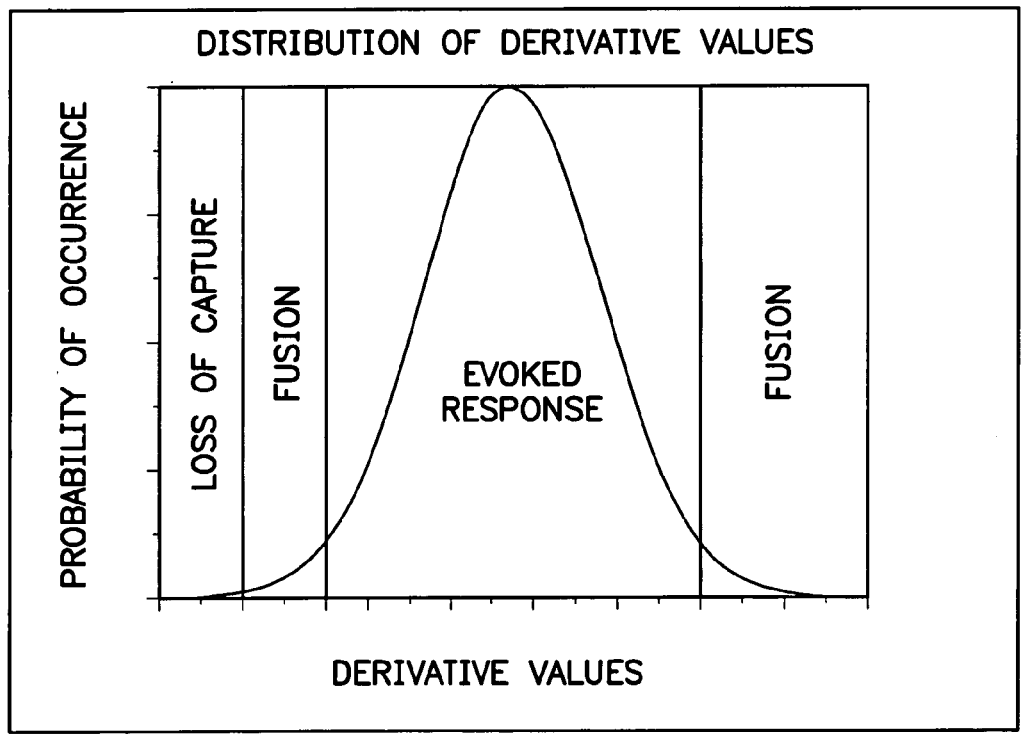
FIG. 7B is a probability distribution plot for derivative values.

FIG. 7B shows a distribution of derivative values, this distribution is for the purpose of illustration and does not correspond to the actual derivative values of FIG. 7A. Actual distributions may under some circumstances have multimodal characteristics, for example, one "mode" corresponding to an evoked response and another "mode" corresponding to fusion. Devices and methods disclosed herein optionally comprise modules capable of using multimodal information to classify cardiac activity and/or determine a pacing therapy. While FIG. 7B shows a probability distribution, a device may rely on a histogram distribution and/or a probability distribution and a user or the device may set parameters (e.g., limits) based on probability or other statistical information. As shown, the distribution has four regions: one Evoked Response region; two Fusion regions; and one Loss of Capture region. A device may adjust the boundaries between these regions or they may be preset. The boundary between the Fusion and Loss of Capture region corresponds to the loss of capture limit shown in FIG. 7A. A device may set the Fusion and Evoked Response boundaries according to user input and/or sensed cardiac activity. In addition, these two boundaries need not be set symmetrically about a mean, median, etc. of the evoked response region (or entire data set). Thus, a device or user may set an upper Fusion region boundary at plus one standard deviation about the mean and set a lower Fusion region boundary at minus two standard deviations about the mean.

Of course, adjustment of these boundaries may, in turn, determine a statistical probability of encountering Fusion or Loss of Capture. The probability distribution may be unique to each patient and hence each patient may have unique boundaries that account for a plethora of health and/or lifestyle conditions. As discussed above, with reference to FIGS. 5A and 5B, statistical methods related to probability allow a user or a device to determine a mode. The mode of a distribution corresponds to the value that occurs most frequently (note that a multimodal distribution has only one mode). Often the mode is different than the median, the mean or the sample mean. The "median" is the value with half the values above it and half the values below it. The "mean" is the average in a traditional sense and it is analogous to the expected value (sum of the values weighted by their probabilities); whereas, "sample mean" is based on sample values. For a derivative method corresponding to the values shown in FIG. 7A, the distribution may not be symmetric, it may be skewed to the left due to loss of capture or to the right (e.g., due to a number of fusion derivative values greater than evoked response derivative values).

Methods disclosed herein optionally include statistical parameters such as variance and standard deviation. Generally, the standard deviation is the square root of the variance. The standard deviation represents an average "distance" of the individual sample "distances" from the mean of the samples. In addition, the standard deviation of the sample mean typically decreases in proportion to the square root of the number of samples (and the variance of the sample mean typically decreases linearly with added samples). Thus, methods disclosed herein optionally maintain statistics (e.g., statistical parameters) based on a fixed number of samples—e.g., including running or moving statistics.

In one exemplary method, a device obtains information related to cardiac activity. The device derives the information to provide a derivative with respect to time value. Next, the device determines at least one statistical parameter based on the derivative value. The device continues to obtain, derive and determine until the statistical parameter satisfies a criterion or criteria. For example, a device may decide to implement the derivative feature if the standard deviation of the samples falls below a limit. Alternatively, the device may decide to implement the derivative feature if a running standard deviation exceeds a limit.

Another statistical method includes cumulative distribution functions. A device or a user may use a cumulative distribution function to determine the probability that an outcome (e.g., a derivative value) will lie between two parameters (e.g., two derivative values). For example, a device or a user may set fusion and loss of capture limits based on probabilities or a probability. According to such a statistical method, a device or user specifies an expected probability of loss of capture. The device or user then uses a distribution of historic information to determine the value that corresponds to that probability. The device then uses the determined value (or parameter) as a loss of capture limit and any integral value falling below that limit will be classified as loss of capture.

Comparison Between Integral and Derivative Methods

Referring to FIGS. 5B and 7B, the integral method has one Fusion region, while the derivative method has two Fusion regions. Referring to FIGS. 5A and 7A, integral and derivative values correspond to the same underlying data. Table 1 shows a comparison of the fusion and loss of capture events for FIGS. 5A and 7A.

TABLE 1

Comparison of Integral and Derivative Methods

| Integral Method | Derivative Method |
|---|---|
| $LOC_1$ | $LOC_1$ |
| $F_1$ | $F_1$ |
| $F_2$ | $F_2$ |
| $F_3$ | $F_3$ |
| $F_4$ | $F_4$ |
| $LOC_2$ | $LOC_2$ |
| $LOC_3$ | $LOC_3$ |
| $F_5$ | $F_5$ |
| $LOC_4$ | $F_6$ |

Of the nine events classified as fusion or loss of capture, the methods differ only as to the last event. The integral method classified the event as loss of capture ($LOC_4$) while the derivative method classified the event as fusion ($F_6$). Referring again to FIGS. 5A and 7A, in particular $F_6$ in FIG. 5a, note that value of this derivative was close to the loss of capture limit. If a user or device desired a higher degree of correspondence between the two methods, then one or both of the loss of capture limits could be adjusted accordingly. Of course, a device or user can optionally adjust the boundaries between the regions shown in FIGS. 5B and 7B.

Combined Integral and Derivative Methods

Figure 8:
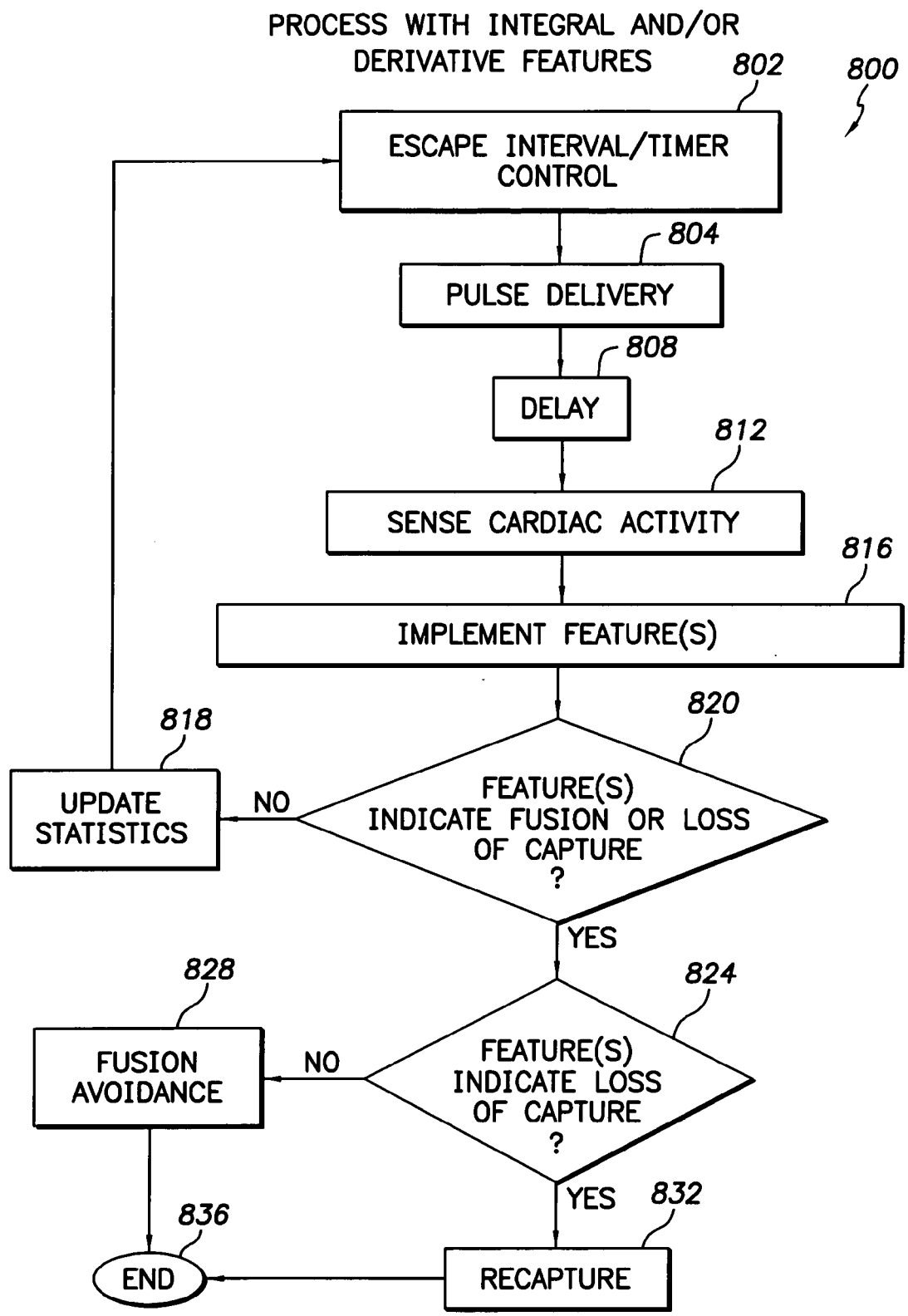
FIG. 8 is a functional block diagram of a process that implements a feature or features, such as, integral and/or derivative methods.

An exemplary process 800 comprising integral and/or derivative features, or methods, is described herein with reference to FIG. 8. Referring to FIG. 8, after an elapsed time corresponding to the pulse delivery rate as determined by the escape interval/timer control circuitry 232 at block 802, a pulse delivery block 804 delivers a pulse to a chamber of the heart. Following delivery, a delay block 808 delays sensing. The delay may correspond to a "blanking interval". In an alternative process, sensing occurs immediately after pulse delivery without a delay. As shown in FIG. 8, after the delay, a sense block 812 commences sensing of cardiac activity. The signal sensed by the device may cover a pre-determined time interval or may cover a time interval determined in real time, e.g., triggered by certain events. A feature implementation block 816 follows the sense block 412; however, in an alternative process, the sensing and feature implementation occur simultaneously. The feature implementation block 816 implements integral and/or derivative features to provide integral, derivative and/or other values related to cardiac activity.

After feature implementation 816, an indication block 820 indicates whether the sensed cardiac activity exhibits fusion or loss of capture characteristics. If the sensed cardiac activity exhibits neither fusion or loss of capture characteristics, then the process 800 enters an update statistics block 818 wherein statistics relevant to implementation of the feature(s) are updated. As discussed herein, statistics include averages, means, indicators of variability, etc.

If the sensed cardiac activity exhibits fusion or loss of capture, then the process 800 enters another indication block 824. The indication block 824 indicates whether the sensed cardiac activity exhibits loss of capture characteristics, for example, an integral value and/or a derivative value that is less than a loss of capture limit. If the block 824 indicates no loss of capture, then the process 800 enters a fusion avoidance block 828. The fusion avoidance block 828 implements one or a variety of fusion avoidance techniques, including, for example, pulse inhibition, positive or negative rate adjustment, and/or AV/PV hysteresis adjustment. To conserve energy, the fusion avoidance block 828 may instruct the device to withhold pulse delivery. As discussed above, the presence of fusion corresponds to intrinsic activity, which typically is sufficient to capture the heart. Under such circumstances, an applied stimulus can waste energy and thereby unnecessarily drain the device's power supply. After the fusion avoidance block 828, the process 800 may terminate at a termination block 836. After termination, the device may simply sense cardiac activity to insure that the intrinsic activity maintains an adequate beat.

If, in the indication block 824, the sensed cardiac activity exhibits characteristics of loss of capture, then a recapture block 832 commences a recapture or autocapture process. After capture has been established, the process 800 optionally terminates at a termination block 836.

A device that implements the aforementioned integral and/or derivative methods may also comprise features that analyze the T-wave signal for purposes of measuring the QT interval, the oxygen saturation level, and other physiological signals (e.g., heart sounds, impedance changes, etc.).

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for operating an implantable stimulation device, comprising:
   obtaining information related to at least one of cardiac depolarization or cardiac contraction using at least one sensor;
   processing the information using a module to provide a value;
   comparing the value with an evoked response parameter and a loss of capture parameter using a microcontroller; and
   implementing a technique in response to the comparing using the stimulation device wherein the technique comprises at least one of capture techniques or fusion avoidance techniques.

2. The method of claim 1, wherein the processing comprises a process selected from the group consisting of integrating using an integration module and deriving using a derivation module.

3. The method of claim 1, wherein the evoked response parameter and the loss of capture parameter comprise statistical parameters.

4. The method of claim 3, wherein the statistical parameters comprise parameters based on historic information related to at least one of cardiac depolarization and cardiac contraction.

5. The method of claim 1, wherein the at least one parameter corresponds to a probability.

6. One or more computer-readable media having computer-readable instructions thereon which, when executed by a programmable stimulation device cause the stimulation device to execute the method of claim 1.

7. A method for operating an implantable stimulation device, the method comprising:
   stimulating heart tissue with stimulation energy;
   obtaining information related to at least one of cardiac depolarization or cardiac contraction;
   integrating the information to provide a value;
   comparing the value with an evoked response parameter and a loss of capture parameter; and
   implementing a technique in response to the comparing wherein the technique comprises at least one of capture techniques or fusion avoidance techniques.

8. The method of claim 7, wherein the obtaining comprises receiving sensor data from at least one sensor positioned in one of the heart and proximal to the heart.

9. The method of claim 7, wherein the integrating comprises integration of at least one of voltage and current information over a time interval.

10. The method of claim 7, wherein the evoked response parameter and the loss of capture parameter comprise statistical parameters.

11. The method of claim 10, wherein the statistical parameters are based on historic information related to cardiac depolarization.

12. The method of claim 7, further comprising storing the value.

13. The method of claim 12, further comprising repeating the obtaining, the integrating and the storing to store a plurality of values.

14. The method of claim 13, further comprising determining a statistical parameter of the plurality of values.

15. The method of claim 7, wherein the evoked response parameter and the loss of capture parameter correspond to probability parameters.

16. One or more computer-readable media having computer-readable instructions thereon which, when executed by a programmable stimulation device, cause the stimulation device to execute the method of claim 7.

17. A method for operating an implantable stimulation device, the method comprising:
   stimulating heart tissue with stimulation energy;
   obtaining information related to at least one of cardiac depolarization or cardiac contraction;
   integrating the information to provide a value;
   comparing the value with an evoked response parameter and a loss of capture parameter; and
   implementing a fusion avoidance technique if the comparison indicates that fusion occurred.

18. The method of claim 17, wherein the evoked response parameter comprises a sample mean of historic integral values minus a product, the product equal to a factor times a calculated deviation corresponding to the sample mean.

19. The method of claim 18, wherein the factor comprises a number between approximately 1 and approximately 6.

20. The method of claim 17, wherein the evoked response parameter comprises a calculated deviation of historic integral values.

21. The method of claim 17, wherein the fusion avoidance technique comprises pulse inhibition.

22. The method of claim 17, wherein integrating the information comprises integrating the information starting at cardiac depolarization.

23. The method of claim 17, wherein integrating the information comprises integrating the information starting at cardiac depolarization and ending at a baseline potential.

24. The method of claim 17, wherein the evoked response parameter corresponds to a probability.

25. One or more computer-readable media having computer-readable instructions thereon which, when executed by a programmable stimulation device, cause the stimulation device to execute the method of claim 17.

26. A method for operating an implantable stimulation device, comprising:
   obtaining information related to at least one of cardiac depolarization or cardiac contraction;
   processing the information to provide at least one value, the at least one value comprising a value selected from the group consisting of integral values and derivative values;
   repeating the obtaining and the processing to provide a plurality of values;
   determining an evoked response parameter and a loss of capture parameter from the plurality of values, the evoked response parameter and the loss of capture parameter comprising statistics;
   obtaining additional information related to at least one of cardiac depolarization and cardiac contraction;
   processing the additional information to provide at least one additional value;
   comparing the at least one additional value to the evoked response parameter and the loss of capture parameter;
   implementing a technique in response to the comparing wherein the technique comprises at least one of capture techniques and fusion avoidance techniques.

27. A cardiac stimulation device comprising:
   a sensor that is operative to obtain information related to at least one of cardiac depolarization or cardiac contraction; and a processor operably coupled to the sensor, the processor being configured to determine a value from the information, the value comprising at least one of an integral value and a derivative value, and being configured to determine a fusion parameter and a loss of capture parameter from the information, the fusion parameter and the loss of capture parameter comprising statistics.

28. The device of claim 27, wherein the parameter corresponds to a probability.

29. The device of claim 27, wherein the processor is configured to compare the value and the parameter.

30. The device of claim 27, wherein the processor is configured to implement a technique, the technique selected from the group consisting of fusion avoidance techniques and capture techniques.

31. An implantable cardiac stimulation device, comprising:

means for obtaining information related to at least one of cardiac depolarization or cardiac contraction; and means for determining a value from the information, the value comprising at least one of an integral value and a derivative value, and determining a fusion parameter and a loss of capture parameter from the information, the fusion parameter and the loss of capture parameter comprising statistics.

32. The device of claim 31, wherein the parameter corresponds to a probability.

33. The device of claim 31, further comprising means for comparing the value and the fusion parameter and the loss of capture parameter.

* * * * *